United States Patent
Lee et al.

(10) Patent No.: US 6,924,368 B2
(45) Date of Patent: Aug. 2, 2005

(54) VARIABLE REGION OF THE MONOCLONAL ANTIBODY AGAINST THE HBV S-SURFACE ANTIGEN AND A GENE ENCODING THE SAME

(75) Inventors: Jong Wook Lee, Kwacheon-Si (KR); In Young Ko, Anyang-Si (KR); Heui Keun Kang, Uiwang-Si (KR); Jung Hyun Nam, Uiwang-Si (KR); Moo Young Song, Suwon-Si (KR); Hyung Jin Moon, Suwon-Si (KR); Tae Hun Song, Suwon-Si (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 10/726,555

(22) Filed: Dec. 4, 2003

(65) Prior Publication Data

US 2004/0191259 A1 Sep. 30, 2004

Related U.S. Application Data

(62) Division of application No. 09/865,483, filed on May 29, 2001, now Pat. No. 6,680,053.

(30) Foreign Application Priority Data

May 29, 2000 (KR) ........................................ 2000-28938

(51) Int. Cl.$^7$ ............................................... C07H 21/04
(52) U.S. Cl. .................. 536/23.53; 536/23.1; 536/23.5; 514/44
(58) Field of Search .............................. 536/23.53, 530, 536/23.1, 23.5; 514/44

(56) References Cited

U.S. PATENT DOCUMENTS 6,589,534 B1    7/2003  Shaul et al. ............. 424/227.1

FOREIGN PATENT DOCUMENTS

KR           10-0250832 B1      1/2000

OTHER PUBLICATIONS

Petit et al., Virology, 180:483–491, 1991.
Shouval et al., Vaccine, 12:1453–1459, 1994.
Neurath et al., Nature, 315:154–156, 1985.
Neurath et al., Vaccine, vol. 4, Mar. 1986, pp. 35–37.

*Primary Examiner*—Laurie Scheiner
(74) *Attorney, Agent, or Firm*—Birch, Stewart, Kolasch & Birch, LLP

(57) ABSTRACT

The present invention relates to a variable region of the monoclonal antibody against the S-surface antigen of hepatitis B virus and a gene encoding the same, a recombinant vector containing the said gene, and a transformant obtained from the said recombinant vector.

7 Claims, No Drawings

VARIABLE REGION OF THE MONOCLONAL ANTIBODY AGAINST THE HBV S-SURFACE ANTIGEN AND A GENE ENCODING THE SAME

This application is a divisional of U.S. Ser. No. 09/865,483, filed May 29, 2001, now U.S. Pat. No. 6,680,053, the entire contents of which are herein incorporated by reference and for which priority is claimed under 35 U.S.C. § 120; and this application claims priority to Application No. 2000-28938 filed in Korea on May 29, 2000 under 35 U.S.C. § 119, the contents of which are herein incorporated by reference.

TECHNICAL FIELD

The present invention relates to a variable region of the monoclonal antibody against S-surface antigen of hepatitis B virus and a gene encoding the same, a recombinant vector containing the said gene, and a transformant obtained from the said recombinant vector.

BACKGROUND ART

Hepatitis B virus (hereinafter, referred to as "HBV"), known as the Dane particle, has a spherical feature of 42 nm diameter. The outer envelope contains a large amount of hepatitis B surface antigens and surrounds the inner nucleocapsid composed of 180 hepatitis B core proteins. The nucleocapsid contains HBV genome, polymerase, etc (Summers et al., Proc. Nat. Acad. Sci, 72, 4579, 1975; Pierre Tiollais et al., Science, 213, 406–411, 1981).

Within the HBV genome, the coding region of HBV surface antigens contains three open reading frame start sites which share a common termination codon producing same S domain. Thus, the HBV surface antigens may be classified into three types, i.e., (1) Small HBV Surface Antigen (hereinafter, referred to as "S-surface antigen"), containing only the S domain, (2) Middle HBV Surface Antigen (hereinafter, referred to as "M-surface antigen"), containing the S domain and an additional 55 amino acid domain known as Pre-S2, and (3) Large HBV Surface Antigen (hereinafter, referred to as "L-surface antigen"), containing the Pre-S1 domain as well as the Pre-S2 and S domain. Among the expressed surface antigens, S-surface antigen is about 80% or more.

Subtypes of S-surface antigen were classified according to their properties of antibody recognition. Antigenic domains expressed in all surface antigen were classified as determinant a. The four other subtypes are d or y and w or r. Determinant d has a lysine at residue 122 while y has arginine. Similarly, determinant w has a lysine at residue 160 while r has arginine (Kennedy R. C. et al., J. Immunol. 130, 385, 1983). Thus, serological types can be classified into four subtypes, such as adr, adw, ayr and ayw (Peterson et al., J. Biol. Chem. 257, 10414, 1982; Lars O. Marnius et al., Intervirology, 38, 24–34, 1995).

The S-surface antigen specifically binds to hepatocyte (Leenders et al., Hepatology, 12, 141, 1990; Irina Ionescu-Matiu et al., J. Med. Virology, 6, 175–178, 1980; Swan N. T. et al., Gastroenterology 80, 260–264, 1981; Swan N. T. et al., Gastroenterology, 85, 466–468, 1983; Marie, L. M. et al., Proc. Nat. Acad. Sci. 81, 7708–7712, 1984). And, it has been identified that human hepatic plasma membrane contains target proteins such as apolipoprotein H and endonexin II which specifically bind to S-surface antigen (Mehdi H. et al., J. Virol., 68, 2415, 1994.; Hertogs K. et al., Virology, 197, 265, 1993).

Meanwhile, in developing an useful therapeutic monoclonal antibody, a humanized antibody is preferable because monoclonal antibodies obtained from mice could cause an immune response when applying to human.

The Korean patent publication No. 1999-8650 has recently disclosed a variable region of the monoclonal antibody against a Pre-S1 epitope which solely exists in a L-surface antigen among the three HBV surface antigens (S-, M-, and L-surface antigens), a gene encoding the same, and a humanized antibody using the same. Because the L-surface antigen is only 1~2% of the expressed surface antigens, however, the L-surface antigen is inappropriate as a target for anti-HBV antibody development for diagnostic as well as therapeutic purposes.

DISCLOSURE OF THE INVENTION

Accordingly, a primary object of the present invention is to provide a gene encoding the variable region of a monoclonal antibody, specifically recognizing the S-surface antigen, especially determinant a, which commonly exists in all of the HBV surface antigens.

It is another object of the present invention to provide a recombinant vector comprising the above gene.

It is a further object of the present invention to provide a transformant obtained using the above recombinant vector.

It is still another object of the present invention to provide a variable region of the above monoclonal antibody.

In accordance with one aspect of the present invention, provided is a gene encoding the monoclonal antibody variable region which specifically recognizes the HBV S-surface antigen.

The present inventors immunize mice with the determinant adr type of S-surface antigen (International Enzymes Inc., USA) which is most frequently found in Korean HBV patients. The spleen cells obtained from the immunized mice were fused with myeloma cells (SP2O-Ag14, ATCC CRL-1581) to generate a large number of hybridoma cells which, following subsequent cloning and selection procedures, eventually give rise to numerous monoclonal antibodies. The present inventors selected monoclonal antibodies specifically binding to the determinant a among the numerous monoclonal antibodies; and as a result, obtained a hybridoma cell line (A9-11-5) producing a distinct monoclonal antibody which specifically binds to the determinant a with high binding affinity.

The present inventors isolated total RNAs from the said hybridoma cell line to synthesize the cDNAs of light and heavy chains, and finally, obtained about 440 bp of light chain cDNA gene comprising SEQ ID NO. 5 and about 460 bp of heavy chain cDNA gene comprising SEQ ID NO. 6, respectively.

From the said monoclonal antibody light and heavy chains, the CDR (complementarity determining region) residues were detected. As a result, it is identified that the CDR residues of the light chain exist at the positions of 23–36, 52–58, and 91–98 representing the peptides of SEQ ID Nos. 9, 10, and 11, respectively. Further, it is found that the CDR residues of the heavy chain exist at the positions of 31–35, 50–65, and 98–103 representing the peptides of SEQ ID Nos. 12, 13, and 14, respectively.

Accordingly, the present invention includes, within its scope, a cDNA encoding a light chain variable region of a monoclonal antibody against a HBV S-surface antigen, the said light chain variable region comprising the peptides of SEQ ID Nos. 9, 10, and 11. Further, the present invention includes a cDNA wherein the light chain variable region has the amino acid sequence of SEQ ID NO. 7, and preferably, a cDNA comprising the nucleotide sequence of SEQ ID NO. 5.

And also, the present invention includes, within its scope, a cDNA encoding a heavy chain variable region of a monoclonal antibody against the HBV S-surface antigen, the said heavy chain variable region comprising the peptides of SEQ ID Nos. 12, 13, and 14. Further, the present invention includes a cDNA wherein the heavy chain variable region has the amino acid sequence of SEQ ID NO. 8, and preferably, a cDNA comprising the nucleotide sequence of SEQ ID NO. 6.

The above cDNA genes encoding the light or heavy chain variable region of a monoclonal antibody may be inserted into plasmid vector such as pCRII (Invitrogen Co. USA) to give recombinant vectors. Accordingly, the present invention includes, within its scope, a recombinant vector pCRA9Lv comprising the above cDNA encoding a light chain variable region and a recombinant vector pCRA9Hv comprising the above cDNA encoding a heavy chain variable region.

Further, microorganisms, such as *E. coli*, may be transformed with the above recombinant vectors, pCRA9Lv and/or pCRA9Hv, to obtain transformants. Accordingly, the present invention includes a transformant *E. coli* DH5α/YRC-pCRA9Lv (KCTC 1011BP) and a transformant *E. coli* DH5α/YRC-pCRA9Hv (KCTC 1010BP) which are transformed with a recombinant vector pCRA9Lv and pCRA9Hv, respectively.

Recombinant vectors may be recovered from the above transformants using known methods (J. Sambrook et al., Molecular cloning, Vol. 1, 1.25–1.28). For example, the cell membrane of a transformant may be weakened with solution 1 (50 mM glucose, 25 mM Tris.HCl, and 10 mM EDTA). With solution 2 (0.2N NaOH and 1% SDS) the cell membrane may be destroyed and proteins and chromosomes may be denatured. The ingredients other than recombinant vectors may be aggregated with solution 3 (5M potassium acetate and acetic acid) and then centrifuged. The obtained recombinant vector layer may be precipitated with ethanol to recover recombinant vectors.

The present invention includes, within its scope, a monoclonal antibody variable region, which consists of a light chain comprising the peptides of SEQ ID Nos. 9, 10, and 11 and a heavy chain comprising the peptides of SEQ ID Nos. 12, 13, and 14. Further, preferable is a monoclonal antibody variable region, wherein the light chain variable region has the amino acid sequence of SEQ ID NO. 7 and the heavy chain variable region has the amino acid sequence of SEQ ID NO. 8.

From the above cDNA genes encoding a monoclonal antibody variable region according to the present invention, a humanized monoclonal antibody against HBV may be obtained by fusing the CDR region where S-surface antigen binds directly (i.e., in case of the light chain, the gene encoding the peptides of SEQ ID Nos. 9, 10, and 11; and in case of the heavy chain, the gene encoding the peptides of SEQ ID Nos. 12, 13, and 14) to a human antibody gene, or by substituting a human antibody variable region with a gene encoding the monoclonal antibody variable region according to the present invention.

As mentioned above, the gene encoding the monoclonal antibody variable region according to the present invention is specifically effective in the recognition of HBV S-surface antigen, especially determinant a, which has the highest expression ratio in the HBV surface antigens. Therefore, the gene according to the present invention may be used to manufacture monoclonal antibodies which may be widely applied to various types of HBV surface antigens, such as adr, adw, ayr and ayw, to neutralize and/or remove HBV.

BEST MODE FOR CARRYING OUT THE INVENTION

The present invention will now be further illustrated in detail by, but is by no means limited to, the following Examples.

EXAMPLE 1

RNA Isolation from the Cell Line (A9-11-5) and its cDNA Synthesis

After 1×108 of A9-11-5 cells were added to 10 ml of 4M guanidinium thiocyanate to disrupt the cells, 8 ml of acidic phenol solution was added thereto. The mixture was centrifuged (10,000 rpm, 10 minutes) to extract the RNA. To 5 μg of the extracted RNA, were added 0.5 ng of oligo d(T), 0.5 unit of RNase inhibitor and 100 unit of moloney murine leukemia virus reverse transcriptase (M-MLV). The resulting mixture was reacted at 37° C. for 1 hour to synthesize cDNA.

Using 2 μg of the synthesized cDNA as a template; in case of the light chain, the DNA oligomers of SEQ ID Nos. 1 and 2 as primers; and in case of the heavy chain, the DNA oligomers of SEQ ID Nos. 3 and 4 as primers, polymerase chain reaction (PCR) was performed with the use of an AmpliTaq polymerase (Perkin-Elmer Biosystem Co., USA). In the first step of the PCR, the reaction was repeated 30 cycles in the reaction conditions of 1.5 minute at 94° C., 2 minutes at 55° C., and 3 minutes at 72° C. In the second step, the reaction was performed 1 cycle in the condition of 1.5 minute at 94° C., 2 minutes at 55° C., and 10 minutes at 72° C.

1.5% Agarose gel electrophoresis was performed using amplified PCR product. After stained with 100 ml of 0.5 μg/ml ethidium bromide solution for 20 minutes, the amplified gene products appeared about 460 bp in case of the heavy chain and about 440 bp in case of the light chain compared to 100 bp of standard DNA ladder (Lifetechnology Co. USA).

EXAMPLE 2 cDNA Cloning

After removing impurities by adding 200 μl of phenol and 200 μl of chloroform to the 440 bp gene fragment (the light chain gene fragment), which was recovered using a dialysis membrane (Spectrum Co. USA) after performing 1.5% agarose gel electrophoresis in Example 1, 2.5 ml of ethanol was added to purify the gene fragment. Purified gene fragment was subcloned into a pCRII vector (Invitrogen Co., USA) and *E.coli* DH5α (Lifetechnology Co., USA) was transformed therewith to give a transformant (Cohen, S. N. et al., Proc. Nat. Acad. Sci. 69, 2110, 1972). The obtained transformant was cultured overnight in the LB medium containing 100 μg/ml of ampicillin and, subsequently, processed to give a plasmid. Then, the plasmid was cut with a restriction enzyme EcoRI (Biolab Co., USA) to give clones Lv-1, Lv-4, and Lv-7 in which the above 440 bp of gene fragment was inserted.

The same procedures were performed with the 460 bp gene fragment (the heavy chain gene fragment) to give a recombinant vector, with which *E.coli* DH5α (Lifetechnology Co., USA) was transformed to obtain a transformant. The transformant was cultured overnight in the LB medium containing 100 μg/ml of ampicillin and subsequently, processed to give a plasmid. Then the plasmid was cut with a restriction enzyme EcoRI (Biolab Co., USA) to give clones Hv-1, Hv-4, and Hv-7 in which the above 460 bp of gene fragment was inserted.

60 μl of polyethylene glycol solution (20% polyethylene glycol and 2.5M NaCl) was added to 100 ug/ml of each plasmid solution obtained from the above clones and then centrifuged. 100 μl of distilled water was added to the resulting precipitate, extracted twice with 50 μl of phenol solution, and 200 μl of ethanol was used to purify plasmids.

5 μl of 2N sodium hydroxide and 10 μl of 10 mM EDTA were added to 50 μl of the solution containing 2 μg of the purified plasmid. Then, the mixture was reacted at 37° C. for 30 minutes. To the reaction mixture, 1 pmol of M13 and T7 primers were added, respectively. The whole mixture was reacted 2 minutes at 65° C., and then allowed to stand to room temperature. The nucleotide sequences of each clone were analyzed using DNA sequenase version II kit (United States Biochemical Co., USA).

As a result, the nucleotide sequences of three light chain clones (Lv-1, Lv-4, and Lv-7) were identical. The plasmid vectors obtained from these clones were named pCRA9Lv. And the transformants with pCRA9Lv plasmid vectors were named *E. coli* DH5α/YRC-pCRA9Lv which was originally deposited in Korean Collection for Type Cultures (KCTC) in Korea Research Institute of Bioscience and Biotechnology, 52, Oun-dong, Yusong-ku, Taejon 305–333, Republic of Korea, on May 16, 2000 (KCTC 18021P) and then, converted to a deposit under the Budapest Treaty on May 16, 2001 (KCTC 1011BP).

Further, the nucleotide sequences of three heavy chain clones (Hv-1, Hv-4, and Hv-7) were identical. The plasmid vectors obtained from these clones were named pCRA9Hv. And the transformants with pCRA9Hv plasmid vectors were named *E. coil* DH5α/YRC-PCRA9Hv which was originally deposited in Korean Collection for Type Cultures (KCTC) in Korea Research Institute of Bioscience and Biotechnology, 52, Oun-dong, Yusong-ku, Taejon 305–333, Republic of Korea, on May 16, 2000 (KCTC 18020P) and then, converted to a deposit under the Budapest Treaty on May 16, 2001 (KCTC 1010BP).

EXAMPLE 3

Nucleotide Sequence Analysis of the cDNA

As a result of analysis on the variable region amino acid sequence (Harris. L. et al., Protein Sci. 4, 306–310, 1995.; Kabat. E. A. et al., Sequence of proteins of immunological interest.5th Ed., 1991.; Williams A. F. et al., Annu. Rev. Immunol. 6, 381–406, 1988) of the monoclonal antibody obtained from the cell line A9-11-5, it was identified that the heavy chain belongs to I(B) subgroup and the light chain belongs to λ 1 series.

Among the variable regions, the antigen-recognition CDR residues of the heavy chain were at the positions of 31–35 (CDR1), 50–65 (CDR2), and 98–103 (CDR3) and those of the light chain were of 23–36 (CDR1), 52–58 (CDR2), and 91–98 (CDR3).

EXAMPLE 4

Binding Affinity of the Monoclonal Antibody Obtained from the Hybridoma Cell Line A9-11-5

$2.0 \times 10^{-11}$M of the monoclonal antibody obtained from the cell line A9-11-5 was added to the solution of the HBV S-surface antigen (International Enzymes Inc., USA) at various concentrations ($1.0 \times 10^{-6} \sim 1.0 \times 10^{-12}$M) and then the mixture was reacted at room temperature for 3 hours.

100 μl of each mixture was added to 96-well immulon plates (Dinatech Co. USA) where 0.1 μg of above S-surface antigen was pre-coated. The mixture was incubated 2 hours at 37° C. and the supernatant solution was removed. 200 μl of 0.5% casein-phosphate buffered saline was added to each well and further incubated 1 hour at 37° C. 100 μl of the diluted (×1,000) goat anti-mouse polyclonal antibody to which horseradish peroxidase was conjugated (Sigma Co., USA) was added, and its optical density was measured using ELISA reader (Dinatech Co., USA).

The monoclonal antibody obtained from the cell line A9-11-5 has high binding affinity of $1.84 \times 10^{-9}$ M-1. The term of binding affinity means that the reciprocal of the antigen concentration at which 50% of monoclonal antibody binding is inhibited (Friguet B. et al., J. of Immunological Method, 77, 305–319, 1985)

While the invention has been described with respect to the specific embodiments, it should be recognized that various modifications and changes may be made by those skilled in the art to the invention which also fall within the scope of the invention as defined as the appended claims.

---

What is claimed is:

1. An isolated cDNA encoding a light chain variable region of a monoclonal antibody against S-surface antigen of hepatitis B virus, said light chain variable region comprising the peptides of SEQ ID Nos. 9, 10, and 11.

2. The isolated cDNA according to claim 1, wherein the light chain variable region has the amino acid sequence of SEQ ID NO. 7.

3. The isolated cDNA according to claim 2, which comprises the nucleotide sequence of SEQ ID NO. 5.

4. A recombinant vector pCRA9Lv comprising the cDNA of claim 1.

5. A transformant E. coli DH5α/YRC-pCRA9Lv (KCTC 1011Bp), which is transformed with a recombinant vector pCRA9Lv.

6. An isolated gene encoding a human antibody light chain comprising a variable region having the amino acid sequence of SEQ ID NO. 7.

7. A human antibody light chain gene having a portion encoding the variable region substituted by a polynucleotide comprising the nucleotide sequence of SEQ ID NO. 5.

* * * * *

SEQUENCE LISTING

<160> NUMBER OF SEQ ID NOS: 14

<210> SEQ ID NO 1
<211> LENGTH: 32
<212> TYPE: DNA
<213> ORGANISM: Artificial Sequence
<220> FEATURE:
<223> OTHER INFORMATION: Primer targeted to the cDNA encoding the light
     chain variable region of the monoclonal antibody against the HBV
     S-surface antigen

<400> SEQUENCE: 1
cccaagctta gctcctcagt ggagggtggg aa                                       32

<210> SEQ ID NO 2
<211> LENGTH: 32

-continued

```
<212> TYPE: DNA
<213> ORGANISM: Artificial Sequence
<220> FEATURE:
<223> OTHER INFORMATION: Primer targeted to the cDNA encoding the light
      chain variable region of the monoclonal antibody against the HBV
      S-surface antigen

<400> SEQUENCE: 2
cccaagctta gctcctcagt ggagggtggg aa                                32

<210> SEQ ID NO 3
<211> LENGTH: 36
<212> TYPE: DNA
<213> ORGANISM: Artificial Sequence
<220> FEATURE:
<223> OTHER INFORMATION: Primer targeted to the cDNA encoding the heavy
      chain variable region of the monoclonal antibody against the HBV
      S-surface antigen

<400> SEQUENCE: 3
actagtcgac atggctgtct tagggctgct cctctg                            36

<210> SEQ ID NO 4
<211> LENGTH: 35
<212> TYPE: DNA
<213> ORGANISM: Artificial Sequence
<220> FEATURE:
<223> OTHER INFORMATION: Primer targeted to the cDNA encoding the heavy
      chain variable region of the monoclonal antibody against the HBV
      S-surface antigen

<400> SEQUENCE: 4
cccaagcttc caggggccag gggatagacg gatgg                             35

<210> SEQ ID NO 5
<211> LENGTH: 327
<212> TYPE: DNA
<213> ORGANISM: Escherichia coli

<400> SEQUENCE: 5
caggctgttg tgactcagga atctgcactc accacatcac ctggtgaaac agtcacactc    60
acttgtcgct caagtactgg ggctattaca actaataact ttgccaactg ggtccaagaa   120
aaaccagatc atttattcac tggtctaata ggtgatacca acaaccgagt tccgggtgtt   180
cctgccagat tctcaggctc cctgattgga gacaaggctg ccctcaccat cacaggggca   240
cagactgaag atgaggcaat atatttctgt gctctatggt acaacaactg ggtgttcggt   300
ggaggaacca aactgactgt cctaggc                                       327

<210> SEQ ID NO 6
<211> LENGTH: 342
<212> TYPE: DNA
<213> ORGANISM: Escherichia coli

<400> SEQUENCE: 6
caggtgcagc tgaagcagtc aggacctggc ctagtgcagc cctcacagag cctgtccatc    60
acctgcacag tctctggttt ctcattaagt acctatggtg tacagtgggt tcgccagtct   120
ccaggaaagg gtctggagtg gctgggagtg atatggagtg gtggaaacac agactataat   180
gcagctttca tatccagact gagcatcagc aaggacaact ccaagaacca agttttcttt   240
aaagtgaaca gtctgcaagc tgatgacaca gccatatatt attgtgccag agcacggtac   300
ttcgatgtct ggggcgctgg gaccacggtc accgtctcct ca                      342
```

<210> SEQ ID NO 7
<211> LENGTH: 109
<212> TYPE: PRT
<213> ORGANISM: Escherichia coli

<400> SEQUENCE: 7

```
Gln Ala Val Val Thr Gln Glu Ser Ala Leu Thr Thr Ser Pro Gly Glu
 1               5                  10                  15

Thr Val Thr Leu Thr Cys Arg Ser Ser Thr Gly Ala Ile Thr Thr Asn
            20                  25                  30

Asn Phe Ala Asn Trp Val Gln Glu Lys Pro Asp His Leu Phe Thr Gly
        35                  40                  45

Leu Ile Gly Asp Thr Asn Asn Arg Val Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Asn Asn
                85                  90                  95

Trp Val Phe Gly Gly Gly Thr Lys Leu Thr Val Leu Gly
            100                 105
```

<210> SEQ ID NO 8
<211> LENGTH: 114
<212> TYPE: PRT
<213> ORGANISM: Escherichia coli

<400> SEQUENCE: 8

```
Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Ser Thr Tyr
            20                  25                  30

Gly Val Gln Trp Val Arg Gln Ser Pro Gly Lys Gly Leu Glu Trp Leu
        35                  40                  45

Gly Val Ile Trp Ser Gly Gly Asn Thr Asp Tyr Asn Ala Ala Phe Ile
    50                  55                  60

Ser Arg Leu Ser Ile Ser Lys Asp Asn Ser Lys Asn Gln Val Phe Phe
65                  70                  75                  80

Lys Val Asn Ser Leu Gln Ala Asp Asp Thr Ala Ile Tyr Tyr Cys Ala
                85                  90                  95

Arg Ala Arg Tyr Phe Asp Val Trp Gly Ala Gly Thr Thr Val Thr Val
            100                 105                 110

Ser Ser
```

<210> SEQ ID NO 9
<211> LENGTH: 14
<212> TYPE: PRT
<213> ORGANISM: Escherichia coli

<400> SEQUENCE: 9

```
Arg Ser Ser Thr Gly Ala Ile Thr Thr Asn Asn Phe Ala Asn
 1               5                  10
```

<210> SEQ ID NO 10
<211> LENGTH: 7
<212> TYPE: PRT
<213> ORGANISM: Escherichia coli

<400> SEQUENCE: 10

```
-continued

Asp Thr Asn Asn Arg Val Pro
1               5

<210> SEQ ID NO 11
<211> LENGTH: 8
<212> TYPE: PRT
<213> ORGANISM: Escherichia coli

<400> SEQUENCE: 11

Ala Leu Trp Tyr Asn Asn Trp Val
1               5

<210> SEQ ID NO 12
<211> LENGTH: 5
<212> TYPE: PRT
<213> ORGANISM: Escherichia coli

<400> SEQUENCE: 12

Thr Tyr Gly Val Gln
1               5

<210> SEQ ID NO 13
<211> LENGTH: 16
<212> TYPE: PRT
<213> ORGANISM: Escherichia coli

<400> SEQUENCE: 13

Val Ile Trp Ser Gly Gly Asn Thr Asp Tyr Asn Ala Ala Phe Ile Ser
1               5                   10                  15

<210> SEQ ID NO 14
<211> LENGTH: 6
<212> TYPE: PRT
<213> ORGANISM: Escherichia coli

<400> SEQUENCE: 14

Ala Arg Tyr Phe Asp Val
1               5
```